(12) United States Patent
Schulze Nahrup et al.

(10) Patent No.: US 8,992,976 B2
(45) Date of Patent: Mar. 31, 2015

(54) PHARMACEUTICAL COMPOSITION CONTAINING DONEPEZIL HYDROCHLORIDE, TABLETS PRODUCED THEREFROM AND METHODS FOR PRODUCING THE SAME

(75) Inventors: Julia Schulze Nahrup, Neuried (DE); Frank Muskulus, Grobenzell (DE); Peter Kraass, Munich (DE)

(73) Assignee: ratiopharm, GmbH, Ulm (DE)

( * ) Notice: Subject to any disclaimer, the term of this patent is extended or adjusted under 35 U.S.C. 154(b) by 1488 days.

(21) Appl. No.: 12/097,596

(22) PCT Filed: Dec. 15, 2006

(86) PCT No.: PCT/EP2006/012122
§ 371 (c)(1),
(2), (4) Date: Jul. 10, 2008

(87) PCT Pub. No.: WO2007/073888
PCT Pub. Date: Jul. 5, 2007

(65) Prior Publication Data
US 2008/0311202 A1    Dec. 18, 2008

(30) Foreign Application Priority Data
Dec. 16, 2005  (DE) .......................... 10 2005 060 377
Aug. 11, 2006  (WO) ................. PCT/EP2006/007990

(51) Int. Cl.
*A61K 9/28*  (2006.01)
*A61K 9/00*  (2006.01)
*C07D 211/06*  (2006.01)
*A61K 9/20*  (2006.01)
*A61K 31/445*  (2006.01)

(52) U.S. Cl.
CPC ............. *A61K 9/2018* (2013.01); *A61K 9/2054* (2013.01); *A61K 9/2059* (2013.01); *A61K 31/445* (2013.01)
USPC ........................... 424/474; 424/400; 546/206

(58) Field of Classification Search
CPC . A61K 31/445; A61K 9/2018; A61K 9/2054; A61K 9/2059; A61K 9/2866; A61K 47/10; A61K 211/32
USPC .................................. 424/474, 400; 546/206
See application file for complete search history.

(56) References Cited

U.S. PATENT DOCUMENTS

| 4,956,182 | A | * | 9/1990 | Bequette et al. .............. 424/476 |
| 5,110,598 | A | * | 5/1992 | Kwan et al. ................... 424/438 |
| 2004/0265372 | A1 | * | 12/2004 | Wynn et al. ................... 424/464 |
| 2004/0265375 | A1 | | 12/2004 | Platteeuw et al. | |
| 2005/0232990 | A1 | | 10/2005 | Boehm et al. | |

FOREIGN PATENT DOCUMENTS

| EP | 1 681 048 | 7/2006 |
| WO | WO 97/46526 | 12/1997 |
| WO | WO 2004/000317 | 12/2003 |
| WO | WO 2005/105054 | 11/2005 |
| WO | WO 2006/045512 | 5/2006 |

OTHER PUBLICATIONS

International Search Report issued by the European Patent Office for PCT/EP06/012122 (Jul. 5, 2007).

* cited by examiner

*Primary Examiner* — Aradhana Sasan
(74) *Attorney, Agent, or Firm* — Chalin A. Smith; Smith Patent (57) ABSTRACT

A pharmaceutical composition is provided according to the invention which is suited for the production of tablets by direct compression and which contains donepezil hydrochloride of polymorphic form I. The polymorphic form I of donepezil hydrochloride in the directly compressed tablet is also stable during long storage.

17 Claims, 7 Drawing Sheets

PHARMACEUTICAL COMPOSITION CONTAINING DONEPEZIL HYDROCHLORIDE, TABLETS PRODUCED THEREFROM AND METHODS FOR PRODUCING THE SAME

This application corresponds to the national phase of PCT Application No. PCT/EP06/012122, filed Dec. 15, 2006, which, in turn, claims priority to German Patent Application No. 10 2005 060 377.7, filed Dec. 16, 2005 and International Patent Application No. PCT/EP06/007990, filed Aug. 11, 2006, the contents of which are incorporated by reference herein in their entirety.

The present invention relates to a pharmaceutical composition which contains crystalline donepezil hydrochloride of polymorphic form I and can be directly compressed into tablets as well as to tablets obtained from this composition by direct compression. In particular, the present invention relates to tablets where the donepezil hydrochloride is stable even during storage and is neither converted into other polymorphic forms nor becomes amorphous.

Donepezil hydrochloride, (+/−)-2,3-dihydro-5,5-dimethoxy-2-[[1-(phenylmethyl)-4-piperidinyl]-methyl]-1H-inden-1-one hydrochloride, is effective as a reversible acetylcholinesterase inhibitor and is used in the treatment of the most different old-age dementias, in particular to prevent and alleviate Alzheimer's disease. The donepezil hydrochloride structure is as follows EP 0 296 560 discloses a number of cyclic amine compounds, which inter alia also comprise donepezil hydrochloride, to treat old-age dementia.

Donepezil hydrochloride has a number of properties which render its formulation in a medicament more difficult. In this connection, the unpleasant taste and a rather low stability, in particular at elevated temperatures, have to be mentioned as examples. There are a plurality of proposals as to how to encounter these problems, reference only being made to WO 98/43675 or WO 00/59544 as an example of the very comprehensive literature.

In connection with donepezil hydrochloride, it is particularly difficult that of the compound an amorphous and also five crystalline polymorphic forms I to V are known, which are disclosed in publications WO 97/046526 and WO 97/046527. These publications also disclose production processes and the characterization of the individual polymorphic forms. The polymorphic forms are to be stable during heating and storage, in particular more stable than the amorphous form. However, it is also known that in particular the physical stability of the polymorphic form I is problematic which during heating and/or storage can be converted into the polymorphic form III.

The conversion of the individual, crystalline, polymorphic forms of donepezil in a medicament, in particular also during the storage, or the conversion of a crystalline form into the amorphous form and vice versa is a problem (the identity of the medicament must be guaranteed during the entire shelf life), and the prior art contains a number of proposals regarding the stabilization of the polymorphic form or the amorphous form of donepezil hydrochloride in a medicament.

For example, EP 1 027 887 discloses pharmaceutical compositions which contain amorphous donepezil hydrochloride and a process for the stabilization thereof by the addition of a crystallization inhibitor.

EP 1 378 238 and WO 2004/071486 disclose pharmaceutical compositions containing donepezil hydrochloride in an amorphous state as a therapeutically active agent to treat dementia or Alzheimer's disease.

Medicaments having the active substance donepezil can be available as comprimates, e.g. as tablets.

The classical method of producing tablets is a granulation process with which using a granulation liquid a granulate is produced which is then compressed into tablets.

A more recent process for the production of tablets is direct compression. In this process, the individual constituents of the composition to be compressed are mixed without previous granulation and then directly compressed. The direct compression is an elegant and simple process; yet it is difficult to obtain with it commercially usable tablets which in addition to a sufficient strength also ensure a sufficiently rapid disintegration. Many active substances cannot be processed by direct compression since they cannot be compressed without a granulation step. Moreover, it is advantageous, in particular with small active substance concentrations, to use a granulation process since this serves for achieving a better distribution of the active substance.

WO 2006/045512, which was published after the priority date of this application, also describes the problem that donepezil hydrochloride must keep its polymorphic form in a drug formulation. WO 2006/045512 solves this problem by formulating either polymorph I or polymorph IV into a solid medicament having a very specific water content ranging from 3 to 10%. The solid medicaments can contain either the donepezil hydrochloride of the polymorphic form I or the donepezil hydrochloride of polymorphic form IV, and the production can be made in any way, one example for the direct compression and several examples for a wet granulation process being given. The example which uses a direct compression does not indicate the polymorphic form of donepezil which is used, and the water content of the produced tablet was 6% by weight.

The object of the invention is to provide a donepezil hydrochloride containing medicament, in which the donepezil hydrochloride is present in a stable, unchanged form even during prolonged storage. In particular, the polymorphic form of donepezil hydrochloride shall not undergo a change.

It has surprisingly been found according to the invention that donepezil hydrochloride of polymorphic form I is not only particularly well suited for direct compression into comprimates, in particular tablets, especially when it is used in small concentrations, but is also stable in a directly compressed comprimate, such as a tablet, during storage and is not converted into another polymorphic form (in particular the form III) nor the amorphous form. As compared thereto, the donepezil hydrochloride of form I is converted into the amorphous form to a considerable extent when it is processed with conventional granulation processes.

The invention thus relates to a pharmaceutical composition, which is suited for the production of comprimates, in particular tablets, by direct compression, containing donepezil hydrochloride of polymorphic form I and comprimates, in particular tablets, which are obtained by direct compression of such a composition, to a process in which the pharmaceutical composition is directly compressed into comprimates, in particular tablets, and to the use of donepezil hydrochloride of polymorphic form I for the production of directly compressed comprimates, in particular tablets.

According to the invention, comprimates are generally understood to mean compressed medicaments, in particular microtablets or tablets. According to the invention the comprimates are preferably tablets. The invention is specified below for tablets; however, the explanations also apply correspondingly to other comprimates, such as microtablets.

A medicament according to the invention where donepezil hydrochloride of polymorphic form I is produced by direct compression, does not require the setting of the water content as indicated in WO 2006/045512. The pharmaceutical compositions according to the invention and the comprimates according to the invention and in particular the tablets according to the invention are therefore not limited as regards their water content. In particular, the pharmaceutical compositions according to the invention and the comprimates according to the invention and in particular the tablets according to the invention may have a water content of less than 6%, preferably of 5.9% or less, more preferably of less than 3%, in particular of 2.9% or less and even more preferably of 2.5% or less.

According to the invention pharmaceutical compositions, comprimates and in particular tablets which have a water of over 10% by weight, in particular of 10.5 by weight to 20% by weight or 10.5% by weight to 15% by weight or of 12% by weight to 18% by weight, are also possible.

The water content is determined according to Karl Fischer, the test being made according to Ph. Eur. 2.5.12, e.g. on a Karl Fischer titrator Metrohm 7012 KF Titrino or an Aqua 40 by ECH. The above percentages and all other percentages in this application are given in % by weight unless otherwise stated expressly or obvious to the person skilled in the art.

Figure 1:
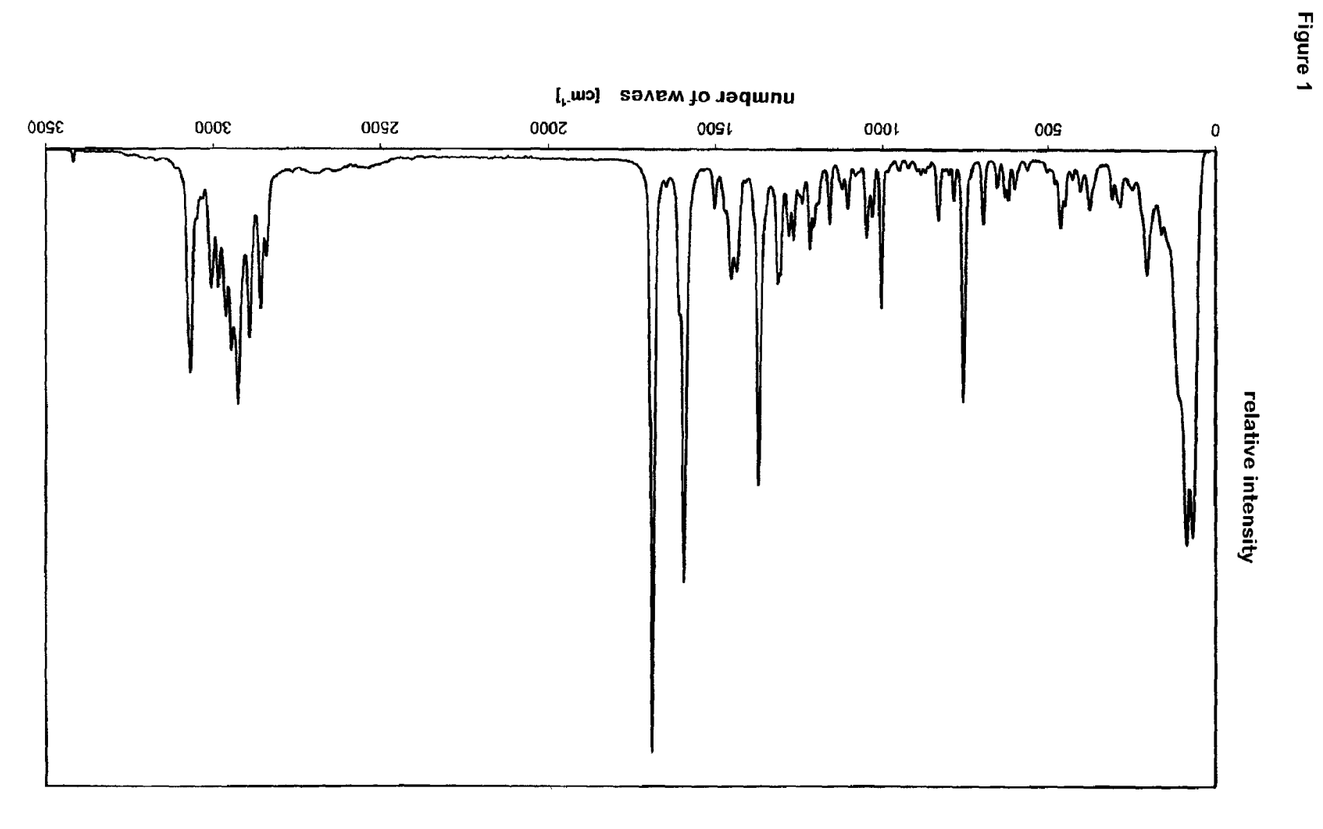
FIG. 1 shows the Raman spectrum of the polymorphic form I of donepezil hydrochloride.
Figure 2:
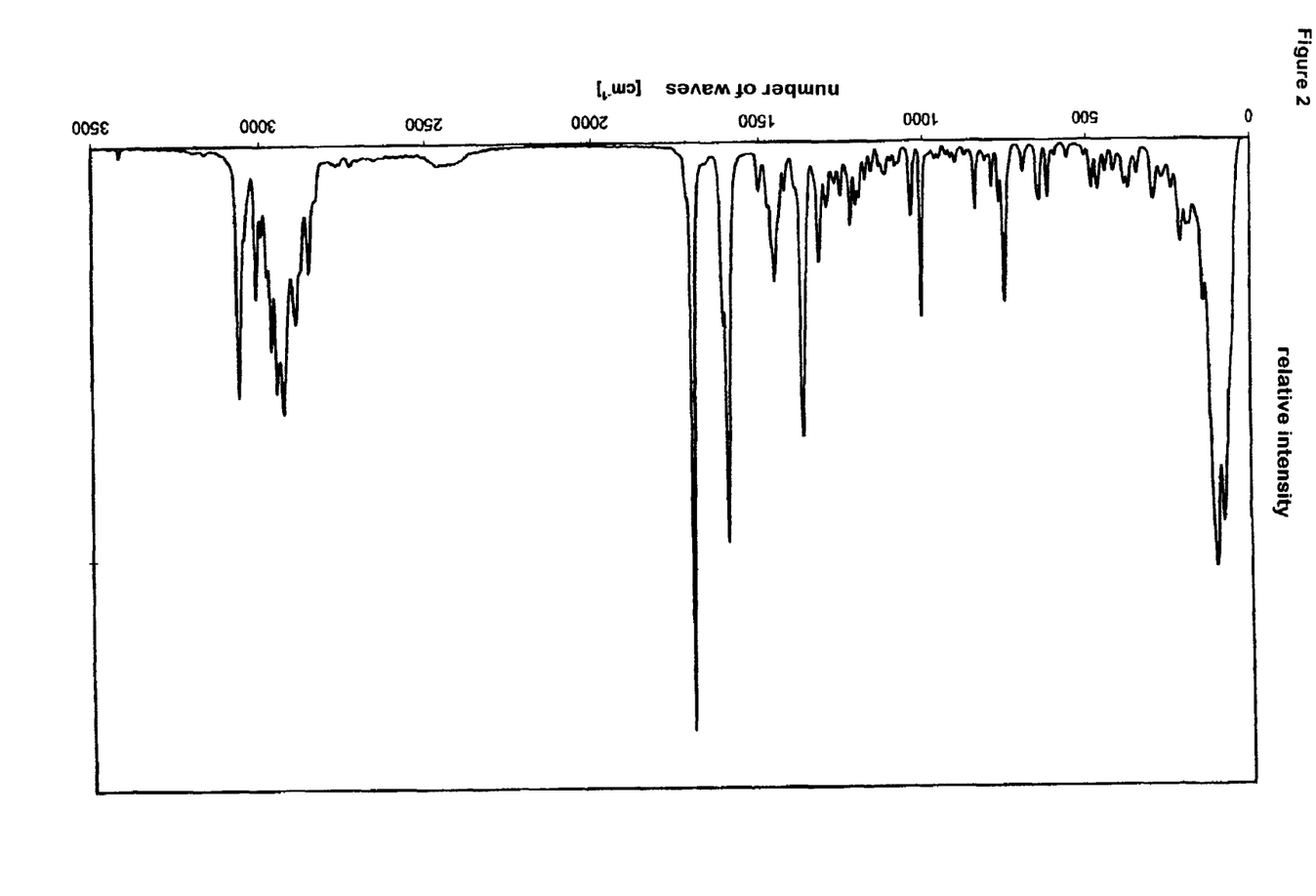
FIG. 2 shows the Raman spectrum of the polymorphic form III of donepezil hydrochloride.
Figure 3:
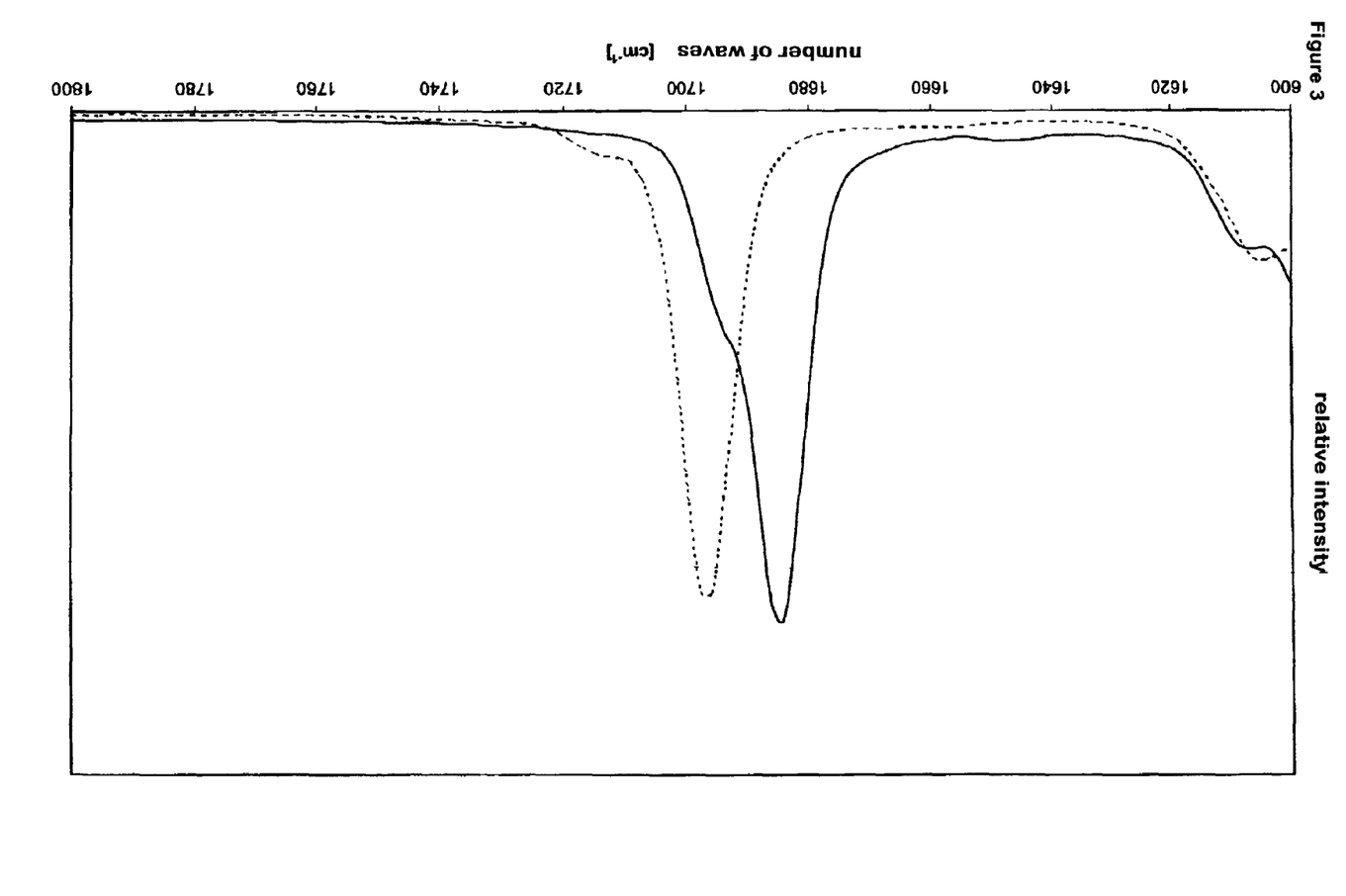
FIG. 3 shows a portion of the Raman spectra of the polymorphic forms I and III of donepezil hydrochloride of 1600 to 1800 cm$^{-1}$, the dashed line showing form III and the continuous line showing form I.

Donepezil hydrochloride of polymorphic form I is known in the prior art, and in this respect reference is made to publications WO 97/046526 and WO 97/046527. In principle, the polymorphic forms of donepezil hydrochloride can be distinguished by X-ray diffractometry, however, in particular when the active substance is compressed into a tablet which is investigated, a distinction is preferably made by $^{13}C$ solid body NMR or more preferably by Raman spectroscopy. The polymorphic forms I and III differ e.g. as regards the Raman spectra in the frequency range of 1600 to 1800 $cm^{-1}$, and the differentiation in this frequency range is usually possible even if conventional tablet excipients are present. The Raman spectra of polymorphic forms I and III of donepezil hydrochloride are shown in FIGS. 1 and 2, and an extension of the range most important for the differentiation of the polymorphic forms in tablets is shown in FIG. 3. When on the basis of this application reference is therefore made to donepezil of polymorphic form I or polymorphic form III, this refers in particular to a donepezil having a Raman spectrum as shown in FIGS. 1 and 2. The significant peaks of the Raman spectra are listed in Table 1 (±2 $cm^{-1}$, only characteristic bands were considered which can be distinguished as regards their position from the corresponding positions of the respectively other form; congruent bands are not listed):

TABLE 1

| Form I | Form III |
| --- | --- |
| 67 $cm^{-1}$ | 110 $cm^{-1}$ |
| 631 $cm^{-1}$ | 644 $cm^{-1}$ |
| 654 $cm^{-1}$ | |
| 755 $cm^{-1}$ | 749 $cm^{-1}$ |
| 831 $cm^{-1}$ | 840 $cm^{-1}$ |

TABLE 1-continued

| Form I | Form III |
| --- | --- |
| 1048 $cm^{-1}$ | 1035 $cm^{-1}$ |
| 1281 $cm^{-1}$ | 1292 $cm^{-1}$ |
| 1306 $cm^{-1}$ | |
| 1435 $cm^{-1}$ | |
| 1684 $cm^{-1}$ | 1697 $cm^{-1}$ |
| 2839 $cm^{-1}$ | 2850 $cm^{-1}$ |
| 2857 $cm^{-1}$ | |
| 2984 $cm^{-1}$ | 2994 $cm^{-1}$ |
| 3005 $cm^{-1}$ | 3009 $cm^{-1}$ |
| 3067 $cm^{-1}$ | 3061 $cm^{-1}$ |

Figure 4:
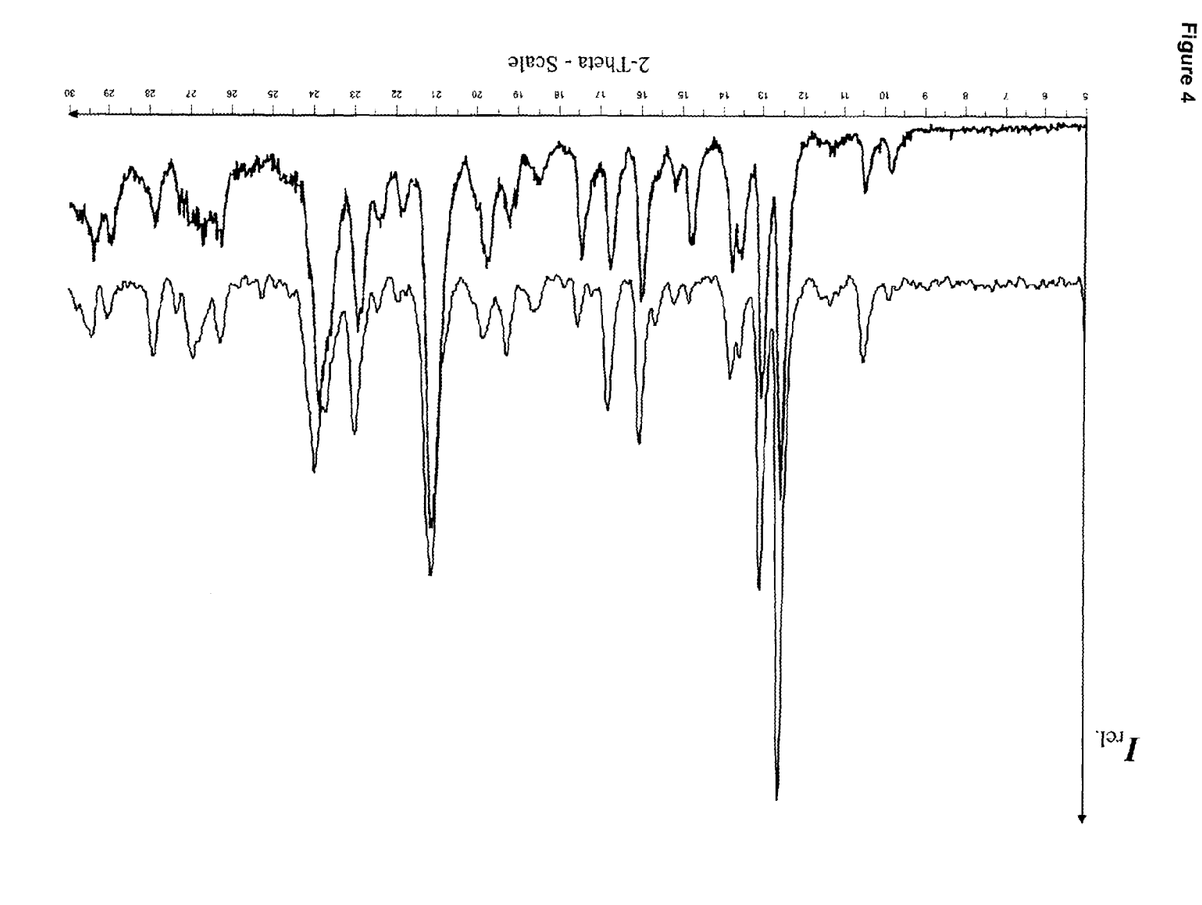
FIG. 4 shows the X-ray diffractograms of two different samples of the donepezil hydrochloride of polymorphic form I, the lower diagram having been taken from WO 97/46527 and the upper diagram having been measured with a sample produced according to the disclosure of this publication.

X-ray diffractograms of two different samples of the form I donepezil hydrochloride are shown in FIG. 4. Table 2 illustrates the automatically prepared peak list of the upper diffractogram of FIG. 4 with an accuracy of ±0.02° 2 theta.

TABLE 2

| 2 Theta | I [%] |
| --- | --- |
| 4.40 | 5 |
| 4.90 | 30 |
| 9.85 | 5 |
| 10.48 | 17 |
| 11.32 | 6 |
| 12.55 | 100 |
| 13.02 | 60 |
| 13.55 | 16 |
| 13.78 | 20 |
| 14.81 | 5 |
| 15.17 | 6 |
| 15.64 | 10 |
| 16.01 | 32 |
| 16.77 | 26 |
| 17.52 | 10 |
| 19.26 | 16 |
| 19.83 | 12 |
| 20.10 | 6 |
| 21.08 | 57 |
| 21.18 | 51 |
| 21.93 | 5 |
| 22.43 | 7 |
| 22.97 | 30 |
| 23.68 | 26 |
| 23.93 | 38 |
| 24.57 | 5 |

Raman spectra indicated in this application were recorded using a spectrometer under the following conditions or settings:
Bruker IFS66 with Raman module FRA 106
Laser: ADLAS DRY 321 (Diode laser pumped Nd: YAG laser)
Wavelength: 1064 nm
Detector: Bruker—D316/8
Number of scans: 500.

Unless otherwise stated or obvious, the instructions for use of the device were observed.

X-ray diffractograms indicated in this application were recorded using a powder diffractometer
STOE transmission diffractometer STADI P (2003-10)
Monochromator: bent germanium monochromator
Detector: IP-PSD (STOE), data detection range 140° 20
Sample carrier: capillary sample carrier
under the following conditions or settings:
Generator: 50 kV, 30 mA
Irradiation: Cu, $K\alpha_1$
Measurement period: 30 minutes
Symmetric detector position, diffractogram folded.

The donepezil hydrochloride of polymorphic form I can preferably be contained in an amount of up to 20% by weight, in particular up to 10% by weight, more preferably 1 to 20% by weight, more preferably 2 to 10% by weight, preferably 2 to 5% by weight, preferably 2.5 to 5% by weight, in the composition according to the invention.

Furthermore, the pharmaceutical composition contains conventional excipients which are suited for the production of tablets by direct compression. Such additives are usually selected from fillers, binders, disintegrants, lubricants and flow regulating agents and where appropriate (but not preferably) further additives.

The pharmaceutical composition according to the invention usually contains over 70% by weight of fillers, in particular 70 to 95% by weight or 70 to 90% by weight, preferably 75 to 95% by weight or 75 to 90% by weight, more preferably 80 to 90 by weight or 85 to 95% by weight.

The content of disintegrants is usually 1 to 25% by weight, preferably 1 to 20% by weight, in particular 2 to 15% by weight. Suitable ranges for the disintegrant content are also 2 to 5% by weight or 7 to 12% by weight, for example.

The lubricant content is usually 0.1 to 2% by weight, preferably 0.2 to 1.5% by weight, in particular 0.2 to 1% by weight.

Formulations which contain the following constituents in the respective quantities are particularly preferred (all data in % by weight).

| Active substance | Filler(s) | Disintegrant | Lubricant |
| --- | --- | --- | --- |
| 1-20 | 70-95 | 1-25 | 0.1-2 |
| 2-10 | 70-95 | 1-20 | 0.1-2 |
| 2-10 | 85-95 | 2-5 | 0.1-2 |
| 2-10 | 70-90 | 1-25 | 0.1-2 |
| 2-10 | 80-95 | 2-15 | 0.1-2 |
| 2.5-5 | 70-95 | 1-20 | 0.1-2 |
| 2.5-5 | 90-95 | 2-5 | 0.1-2 |
| 2.5-5 | 70-90 | 2-25 | 0.1-2 |
| 2.5-5 | 80-95 | 2-15 | 0.1-2 |

If the composition comprises a flow regulating agent, it is usually present in a quantity of 0.1 to 5% by weight, preferably 0.5 to 5% by weight, preferably 1 to 4 by weight, in particular 2 to 3% by weight.

One or more compounds which supply part of the material serving for achieving the necessary and desired total tablet composition can be used as fillers. Inter alia microcrystalline cellulose is usable in different particle sizes, in particular with a mean particle size ranging from 20 µm to 200 µm, in particular ranging from 50 µm to 150 µm, such as about 100 µm, such as the known Avicel® products, e.g. Avicel® PH-102. Further suitable fillers are e.g. lactose, cellactose (a mixture of cellulose and lactose), calcium phosphate, dextrose, mannitol, maltodextrin, isomalt and where appropriate also sorbitol or saccharose. When the fillers are selected, care is to be taken that grades are used which are suited for the direct compression of tablets. This is indicated in the commercial products by the respective manufacturers or can be checked by simple experiments. The most preferred filler is microcrystalline cellulose commercially available under the tradenames Avicel®, Vivapur®, and Emcocel®, for example.

More preferred fillers are fillers rich in water, such as calcium sulfate dihydrate, which is commercially available under the designation of compactrol, for example, calcium chloride dihydrate or magnesium trisilicate.xH$_2$O.

Along with the above fillers, in particular also mannitol, sorbitol, isomalt, maltitol and lactitol anhydrate are preferred as fillers, the filler mannitol being very much preferred according to the invention. For example, the quality Pearlitol® 400 DC is well suited.

The most preferred filler according to the invention is a mixture of microcrystalline cellulose, such as in particular microcrystalline cellulose and mannitol. This mixture is preferred especially when inventive pharmaceutical compositions, comprimates and in particular tablets are to be provided which are to have a small water content, in particular a water content of less than 3%, in particular of 2.9% or less and more preferably of 2.5% or less.

The ratio of microcrystalline cellulose to mannitol is not particularly limited. However, it is preferred to use more mannitol than microcrystalline cellulose and the ratio ranges preferably from 1:1.1 to 1:5, more preferably from 1:2 to 1:4. All indications as to the "ratios" based on this application refer to weight ratios unless otherwise stated or readily obvious to a person skilled in the art.

With respect to formulations rich in water, i.e. comprimates such as tablets and microtablets having a water content of over 10% by weight, in particular of 10.5 by weight to 20% by weight or 10.5% by weight to 15% by weight or 12% by weight to 18% by weight, fillers rich in water are particularly preferred, such as calcium sulfate dihydrate, which is commercially available under the designation of compactrol, calcium chloride dihydrate or magnesium trisilicate.xH$_2$O. These fillers rich in water are usually used in admixture with other fillers, in particular with microcrystalline cellulose such as the Avicel® products, e.g. with Avicel® PH 102. The ratio of other filler, such as microcrystalline cellulose (in particular of Avicel® PH 102), to water containing filler (such as calcium sulfate dihydrate, calcium chloride dihydrate or magnesium silicate.xH$_2$O) is not particularly limited; however, it is preferred to use more filler rich in water than other filler, such as microcrystalline cellulose, and the ratio preferably ranges from 1:1.1 to 1:5, more preferably it is about 1:2 or also ranges from 1:1.5 to 1:3.

Disintegrants suited for the direct compression are known in the prior art. Disintegrants are also referred to as "disintegrators". Disintegrants preferred according to the invention are e.g. crospovidone (Collidon® CL) and starch or preagglutinated starch, in particular the commercial product "Starch 1500®". Further suitable starches are commercially available under the designations of Lycatab® PGS, Prejel® and Sepistab® ST 200, for example. In addition, the known so-called "super disintegrants" can also be used, such as croscarmellose sodium (e.g. Ac-Di-Sol® and others) and carboxymethyl starch sodium (e.g. Explotab®, Primojel® and others). Starches such as Starch 1500® are particularly preferred.

According to the invention the composition can contain as a lubricant one or more compounds supporting the production and processing of the tablet. Usable lubricants are inter alia stearic acid and the derivatives thereof, such as calcium stearate, and in particular sodium stearyl fumarate (which is commercially available under the designation of Pruv®, for example) and magnesium stearate, glycerolmono-, glyceroldi- and in particular glyceroltristearate, hydrogenated vegetable oil (e.g. Lubritab®, Dynasan®, Sterotex®) or a polyethylene glycol (e.g. Lutrol®, Carbowax®).

Where appropriate, the pharmaceutical composition according to the invention can comprise one or several flow regulating agents. Suitable flow regulating agents are magnesium trisilicate, talc and in particular silicon dioxide (e.g. Aerosil®, in particular Aerosil® 200).

The pharmaceutical compositions according to the invention can contain further conventional, pharmaceutically compatible additives and excipients; they preferably contain no further excipients apart from the above ones (filler, disintegrant, lubricant and flow regulating agent, where appropriate).

Some fillers, such as microcrystalline cellulose, may also serve as a binder. Therefore, fillers having a binder function are also counted among the fillers based on this application.

The tablet according to the invention is obtained by direct compression of the pharmaceutical composition containing donepezil hydrochloride of polymorphic form I.

The tablet can be film-coated with one or several coating agents. Usable coating agents are hypromellose (hydroxypropyl methylcellulose), polyvinyl alcohol, sodium carboxymethylcellulose and various methacrylic acid polymers (Eudragit®), hypromellose and in particular eudragite being preferred. The tablets are coated as usual. In addition to the coating agent, the coating may contain further conventional constituents of tablet coatings, such as polyethylene glycol (PEG), talc or titanium dioxide and also lactose, where appropriate.

The process for the production of the tablets by direct compression of the pharmaceutical composition containing donepezil hydrochloride of polymorphic form I can be carried out as follows, for example:
1) Charging the filler, e.g. microcrystalline cellulose, adding the donepezil hydrochloride and thereafter or simultaneously the other constituents, such as disintegrants and, where appropriate, flow regulating agents, with the exception of the lubricant, followed by mixing. The mixing can be carried out in a conventional mixer, e.g. in a container mixer. The mixing time and rate are chosen as a function of the mixer used to ensure adequate mixing. Typical mixing times in a container mixer range from 5 to 30 minutes at 10 to 40 revolutions per minute.
2) Deagglomerating the premix from donepezil hydrochloride of polymorphic form I and fillers and disintegrants as well as, where appropriate, further excipients, by a suitable screen, in particular in the screen range of 400 mm to 800 mm, such as a 0.600 mm screen
3) Carrying out another mixing step
4) Adding the deagglomerated lubricant (e.g. screen the same as in 2)) and carrying out another mixing step
5) Compressing the mixture into tablets
6) Where appropriate, film coating the tablet with one or several coating agents as usual.

The tablet weight is not particularly limited, tablets having 100 to 600 mg, e.g. 100 to 200 mg or also 200 to 300 mg or 300 to 400 mg, are conventional.

The following embodiments are particularly preferred according to the invention:
1. A pharmaceutical composition which is suited for the production of comprimates, in particular tablets, by direct compression and contains donepezil hydrochloride of polymorphic form I.
2. The pharmaceutical composition according to embodiment 1, characterized in that it contains up to 20% by weight of donepezil hydrochloride of polymorphic form I.
3. The pharmaceutical composition according to embodiment 2, characterized in that it contains 2 to 10% by weight of donepezil hydrochloride of polymorphic form I.
4. The pharmaceutical composition according to embodiment 2 or 3, characterized in that it contains 70% by weight or more of a filler, 5 to 25% by weight of a disintegrant, 0.1 to 2% by weight of a lubricant and, where appropriate, 0.1 to 5% by weight, preferably 0.5 to 5% by weight, of a flow regulating agent.
5. The pharmaceutical composition according to any of embodiments 1 to 4, characterized in that the comprimate is a tablet.
6. A comprimate, obtainable by direct compression of a pharmaceutical composition according to any of embodiments 1 to 5.
7. The comprimate according to embodiment 6, which is coated with one or several coating agents.
8. The comprimate according to embodiment 6 or 7, which is a tablet.
9. A process for the production of comprimates containing donepezil hydrochloride, characterized in that a pharmaceutical composition according to any of embodiments 1 to 5 is directly compressed.
10. The process according to embodiment 9, wherein the comprimates are tablets.
11. Use of donepezil hydrochloride of polymorphic form I for the production of comprimates by direct compression.
12. Use according to embodiment 10, wherein the comprimates are tablets.
13. The pharmaceutical composition according to any of embodiments 1 to 8, characterized in that the composition has a water content of less than 6%, preferably of 5.9% or less, more preferably of 2.5% or less.
14. The pharmaceutical composition according to any of embodiments 1 to 8, characterized in that the composition has a water content of over 10% by weight, in particular of 10.5% by weight to 20% by weight, in particular of 10.5% by weight to 15% by weight or of 12% by weight to 18% by weight.
15. The pharmaceutical composition according to embodiment 13, characterized in that it contains a mixture of microcrystalline cellulose and mannitol as a filler.
16. The pharmaceutical composition according to embodiment 14, characterized in that it contains as a filler a mixture of microcrystalline cellulose and one or several fillers selected from calcium sulfate dihydrate, calcium chloride dihydrate and magnesium trisilicate.xH$_2$O.

The following examples explain the invention:

EXAMPLE 1

Donepezil hydrochloride of polymorphic form I was produced in accordance with the disclosure of WO 97/46527. The X-ray diffractogram is shown in FIG. 4 (top diagram) and the essential peak positions are shown in Table 2. A pharmaceutical composition which was suited for direct compression was produced with the constituents of the following table.

| Constituent | Composition in mg/tablet |
| --- | --- |
| Donepezil hydrochloride | 10 |
| Starch (starch® 1500) | 28.00 |
| Avicel® PH-102 | 64.00 |
| Tablettose® 70 (lactose monohydrate) | 176.60 |
| Magnesium stearate | 1.4 |

The pharmaceutical composition was prepared as follows:
1) Sieving the donepezil hydrochloride of polymorphic form I by a 0.355 mm screen,
2) charging Avicel® PH-102 and adding donepezil and the starch and then the other substances with the exception of magnesium stearate, carrying out a premixing step for 5 minutes in a Turbula T 10B mixer which has a 1 liter drum (manufacturer Willy A. Bachofen) and a mixing speed of 23 revolutions per minute, deagglomerated by means of a 0.8 mm screen, and carrying out a remixing step for 15 minutes in the same mixer at equal speed,
3) deagglomerating magnesium stearate by a 0.355 mm screen, adding it to mixture 2) and carrying out a mixing step in the same mixer for 3 minutes.

The resulting composition was directly compressed as usual into 9 mm biconvex tablets having a tablet weight of 280 mg using a KorschEKO tablet press.

Figure 5:
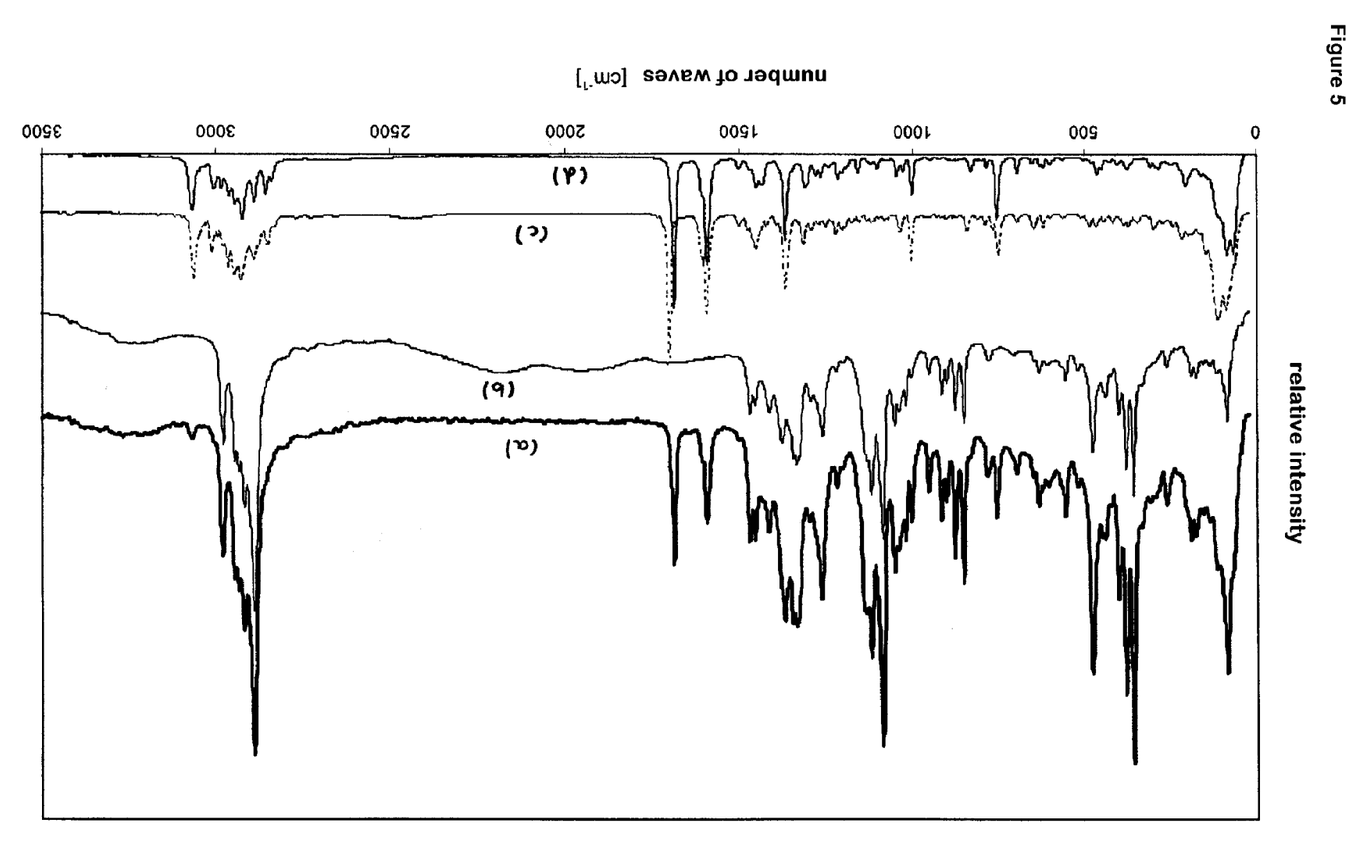
FIG. 5 shows the following Raman spectra from top to bottom: Tablet according to Example 1 of the invention after 8 months of closed storage under stress conditions at 30° C. and 65% relative humidity (a), active substance free tablet (b) in other respects identical with (a), donepezil hydrochloride of polymorphic form III (c) and donepezil hydrochloride of the polymorphic form I (d)
Figure 6:
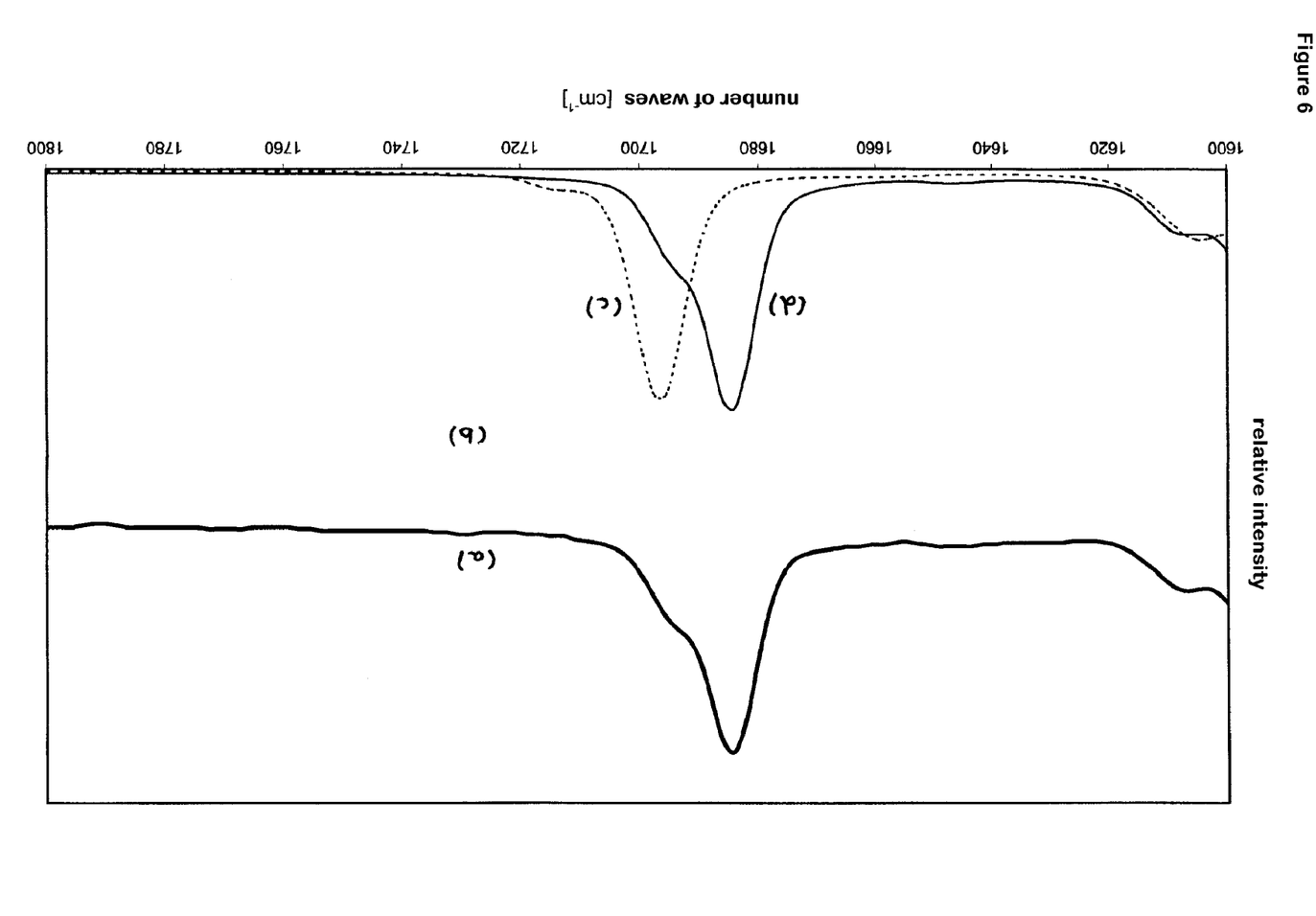
FIG. 6 shows the relevant section of the Raman spectrum of FIG. 5, enlarged in the region of 1600 to 1800 cm$^{-1}$.

The thus produced tablets were stored in a closed fashion at 30° C. and 65% relative humidity (stress conditions) for 8 months and then investigated by means of Raman spectroscopy. The spectra are given in FIGS. 5 and 6. It turns out that even after 8-month storage under stress conditions the donepezil hydrochloride is still present without change in the polymorphic form I while essential amounts of the amorphous form or the polymorphic form III could not be detected. The spectrum corresponded to the Raman spectrum (not shown) made directly after the production.

By means of $^{13}$C-NMR spectra it can also be shown that the polymorphic form I of donepezil hydrochloride does not change during storage.

COMPARATIVE EXAMPLE 1

A granulate was made as usual from the constituents indicated in the following table

| Constituent | Composition in mg/tablet |
| --- | --- |
| Donepezil hydrochloride | 4.97 |
| Starch® 1500 | 11.95 |
| Avicel® PH102 | 65.00 |
| Tablettose® 70 | 32.50 |
| Aerosol® 200 | 10.80 |
| Pharmacoat® 603 | 3.75 |
| Pruv® | 1.00 |
| Water | As required | and then compressed into tablets.

Figure 7:
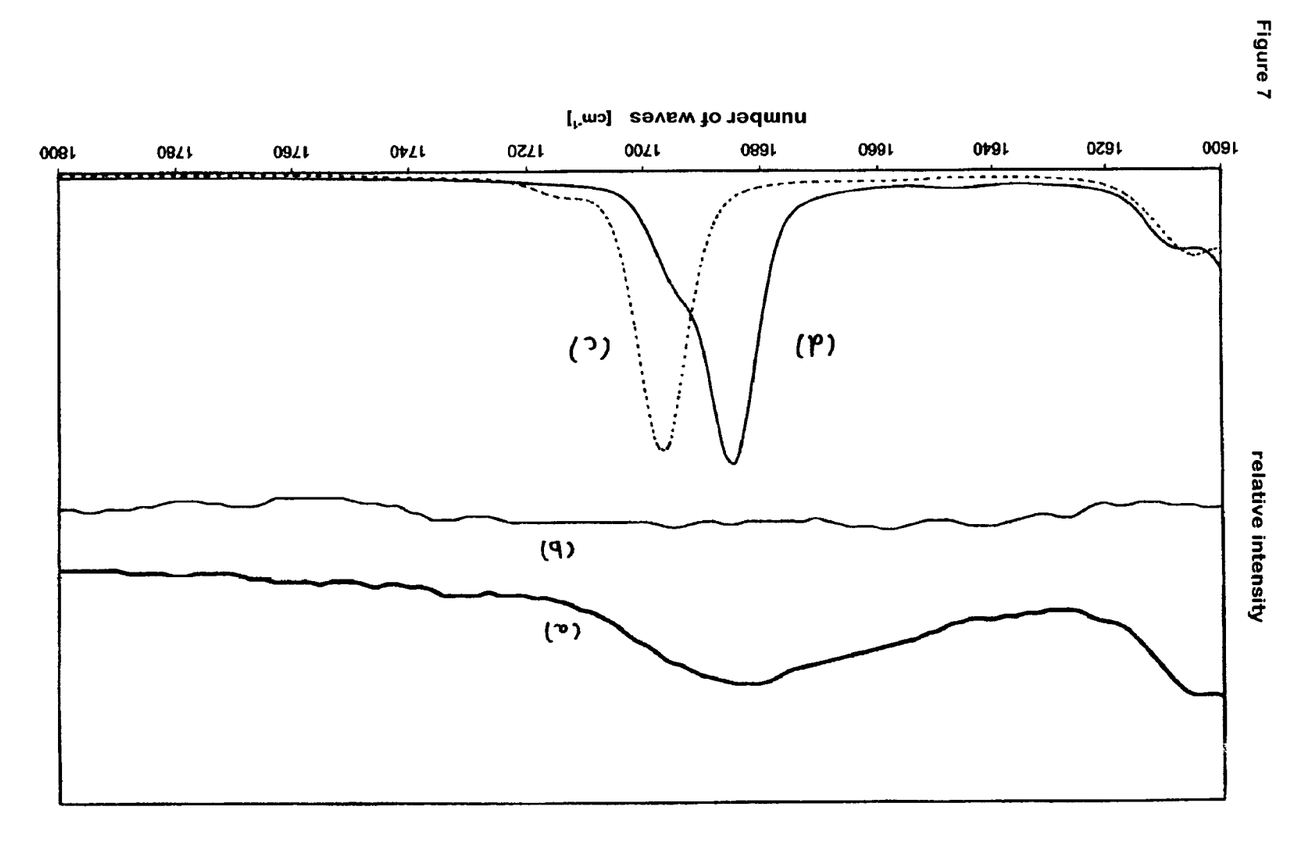
FIG. 7 shows the following Raman spectra from top to bottom, only the enlarged region of 1600 to 1800 cm$^{-1}$ being shown each: Tablet according to Comparative Example 1 directly after the production (a) active substance free tablet (b) in other respects identical with (a) donepezil hydrochloride of polymorphic form III (c) and donepezil hydrochloride of polymorphic form I (d).

The thus produced tablets were investigated directly after the production by Raman spectroscopy and the relevant part of the spectrum is shown in FIG. 7. It turns out that even directly after the production all or at least relevant parts of donepezil hydrochloride of polymorphic form I were converted into amorphous donepezil hydrochloride. The storage of the tablets was superfluous under these circumstances.

EXAMPLE 2

Tablets were made as follows from the below constituents:

| No. | Constituents | 5 mg [mg] tablets | 7.5 mg [mg] tablets | 10 mg [mg] tablets |
| --- | --- | --- | --- | --- |
| 1 | Donepezil-HCl Polymorph I | 5.0 | 7.5 | 10.0 |
| 2 | Avicel® PH102 Microcrystalline cellulose | 117.9 | 176.9 | 235.8 |
| 3 | Starch® 1500 Pregelatinized starch | 5.0 | 7.5 | 10.0 |
| 4 | Magnesium stearate | 0.4 | 0.6 | 0.8 |
| 5 | Total | 128.3 | 192.5 | 256.6 |

1. Avicel® PH102 was charged and then the donepezil hydrochloride and starch 1500 were added and mixed in a container mixer at 23 revolutions per minute for 9 minutes.
2. The mixture was deagglomerated by a 0.600 mm screen, and another mixing step was carried out at 23 revolutions per minute for 22 minutes.
3. Magnesium stearate was also deagglomerated by a 0.600 mm screen and added to the mixture. The mixture was again mixed at 23 revolutions per minute for 4 minutes.
4. The mixture was excellently compressed into tablets, in particular as regards the 5 mg tablets having a height of 3.35±0.20 mm and a hardness of 120 N±10 N. The tablet showed a rapid and excellent release profile. As in Example 1, it turns out during storage that the donepezil hydrochloride of polymorphic form I is physically stable in the tablet.

EXAMPLE 3

The following uncoated tablets were prepared in a way substantially equal to that described in Example 2:

| No. | Constituents | 5 mg [mg] tablets | 7.5 mg [mg] tablets | 10 mg [mg] tablets |
| --- | --- | --- | --- | --- |
| 1 | Donepezil-HCl Polymorph I | 5.0 | 7.5 | 10.0 |
| 2 | Avicel® PH102 Microcrystalline cellulose | 86.6 | 129.9 | 173.2 |
| 3 | Tablettose® 80 Lactose monohydrate | 25.0 | 37.5 | 50.0 |
| 4 | Starch® 1500 Pregelatinized starch | 13.0 | 19.5 | 26.0 |
| 5 | Magnesium stearate | 0.4 | 0.6 | 0.8 |
| 6 | Total | 130.0 | 195.0 | 260.0 |

The mixture could excellently be compressed into tablets, in particular with respect to the 5 mg tablets having a height of 3.50±0.20 mm and a hardness of 70 N±10 N. The tablet showed a rapid and excellent release profile. As in Example 1, it turned out during storage that the donepezil hydrochloride of polymorphic form I is physically stable in the tablet.

EXAMPLE 4

Each of the tablets of Examples 1, 2 and 3 was coated with the following coating systems as usual:
a) hypromellose, titanium dioxide, polyethylene glycol, talc, lactose
b) hypromellose, titanium dioxide, polyethylene glycol, talc.

EXAMPLE 5

Corresponding to Example 1, further tablets having a weight of about 280 mg were prepared. The accurate compositions are listed in the following table:

| No. | Donepezil HCl | Starch 1500® | Pearlitol® 400 DC | Avicel® PH 102 | Isomalt® DC | Tablettose® 70 | Dextrose Roferose® G | Emdex® | Magnesium stearate |
|---|---|---|---|---|---|---|---|---|---|
| 1 | 10.00 | 28.00 | | 240.60 | | | | | 1.40 |
| 2 | 10.00 | 28.00 | | 64.00 | | 176.60 | | | 1.40 |
| 3 | 10.00 | 28.00 | | 64.00 | | | 176.60 | | 1.40 |
| 4 | 10.00 | 28.00 | | 64.00 | | | | 176.60 | 1.40 |
| 5 | 10.00 | 28.00 | | 64.00 | 176.60 | | | | 1.40 |
| 6 | 10.00 | 28.00 | 176.60 | 64.00 | | | | | 1.40 |

For the production of the tablets, the donepezil hydrochloride (polymorphic form I) was sieved in particular by a 0.355 mm screen. Avicel® was added, then the donepezil hydrochloride and thereafter the other substances without the magnesium stearate were admixed, and the mixture was mixed in the Turbula mixer (1 l vessel) for 5 minutes. The mixture was sieved by a 0.8 mm screen, returned into the mixing vessel and mixed for another 15 minutes. The magnesium stearate was sieved by 0.355 mm, and a mixing step was carried out for another 3 minutes. The mixture was compressed into 9 mm biconvex tablets on a KorschEKO press.

The tablets showed an excellent breaking strength, friability and an excellent disintegration period of usually less than one minute.

EXAMPLE 6

Corresponding to Example 1, tablets having a weight of about 280 mg per item were made from the following constituents:

| | |
|---|---|
| Donepezil-HCl (polymorphic form I) | 10 mg |
| Starch 1500® | 28 mg |
| Avicel® PH 102 | 64 mg |
| Pearlitol® 400 DC | 176.60 mg |
| Magnesium stearate | 1.40 mg |

The water content of the resulting tablets was determined at 130° C. according to Karl Fischer and it was 2.1±0.1%.

The tablets showed an excellent breaking strength, friability and an excellent disintegration period of usually less than 1 minute. The active substance release (900 ml 0.1 mol HCl, pH 1.0, 37° C., 50 revolutions per minute, USP Paddle device) was over 80% after 5 minutes.

EXAMPLE 7

Corresponding to Example 1, tablets having a weight of 129.8 mg/item were made from the following constituents:

| | |
|---|---|
| Donepezil-HCl | 5 mg |
| Ac-di-sol® | 6 mg |
| Avicel® PH 102 | 27.82 mg |
| Magnesium stearate | 1.2 mg |
| Mannitol 60 | 89.78 mg |

The water content of the resulting tablets was determined at 130° C. according to Karl Fischer, and it was 1.5%.

The tablets showed an excellent breaking strength, friability and an excellent disintegration period of usually less than 1 minute. After 3 weeks of storage at 50° C. and 75% relative humidity in a closed glass vessel, no change in the polymorphic form was detected. Only donepezil hydrochloride of polymorphic form I continued to be present.

EXAMPLE 8

According to Example 1, tablets having a composition as indicated in the following table were prepared. The donepezil hydrochloride was of polymorphic form I:

| No. | Donepezil HCl (mg) | Starch 1500® (mg) | Avicel® PH 102 (mg) | Compactrol® (Calciumsulfate dihydrate) (mg) | Calciumchlorate dihydrate (mg) | Magnesium trisilicate·$xH_2O$ (mg) | Aerosil® 200 (mg) | Magnesium stearate (mg) | Ac-disol® (mg) | Primojel® (mg) | Water content |
|---|---|---|---|---|---|---|---|---|---|---|---|
| 1 | 5 | 13 | 37.19 | 74.21 | — | — | 1.25 | 0.4 | — | — | 14 |
| 2 | 5 | — | 37.15 | 80 | — | — | 1.25 | 0.4 | 6 | — | 14.1 |
| 3 | 5 | — | 44.19 | — | 74.21 | — | — | 0.4 | 6 | — | 16.8 |
| 4 | 5 | — | 44.19 | — | 74.21 | — | — | 0.4 | 6 | — | 16.9 |
| 5 | 5 | — | 37.19 | — | 74.21 | — | — | 0.4 | 13 | — | 17.3 |
| 6 | 5 | — | 44.19 | — | 74.21 | — | — | 0.4 | — | 6 | 17.0 |
| 7 | 5 | 13 | 37.19 | — | — | 74.21 | 0.75 | 0.4 | — | — | 13.4 |
| 8 | 5 | 13 | 37.19 | — | — | 74.21 | 0.75 | 0.4 | — | — | — |
| 9 | 5 | — | 37.19 | — | — | 80.46 | 0.75 | 0.4 | 6 | — | — |

The water content was determined at 130° C. according to Karl Fischer. The tablets showed an excellent breaking strength, friability and an excellent disintegration period of usually less than 1 minute. After 3 weeks under the storage conditions indicated in Example 7 (3 weeks at 50° C. in the closed glass vessel), no conversion from polymorph I into another polymorph or the amorphous form was detected. The chemical stability was very good.

The invention claimed is:

1. A pharmaceutical composition, suited for the production of comprimates by direct compression, said composition containing 2 to 10% by weight donepezil hydrochloride of polymorphic form I characterized by Raman peaks at 67 $cm^{-1}$, 631 $cm^{-1}$, 654 $cm^{-1}$, 755 $cm^{-1}$, 831 $cm^{-1}$, 1048 $cm^{-1}$, 1281 $cm^{-1}$, 1306 $cm^{-1}$, 1435 $cm^{-1}$, 1684 $cm^{-1}$, 2839 $cm^{-1}$, 2857 $cm^{-1}$, 2984 $cm^{-1}$, 3005 $cm^{-1}$, and 3067 $cm^{-1}$, wherein said composition further contains a filler comprising microcrystalline cellulose.

2. The pharmaceutical composition according to claim 1, wherein said composition contains 70% by weight or more of said filler, 5 to 25% by weight of a disintegrant, 0.1 to 2% by weight of a lubricant and, optionally, 0.1 to 5% by weight of a flow regulating agent.

3. The pharmaceutical composition according to claim 1, wherein the comprimate is a tablet.

4. A comprimate obtained by direct compression of a pharmaceutical composition according to claim 1.

5. The comprimate according to claim 4, wherein said comprimate is coated with one or several coating agents.

6. The comprimate according to claim 4, wherein said comprimate is a tablet.

7. A process for the production of comprimates containing donepezil hydrochloride, comprising the step of directly compressing a pharmaceutical composition according to claim 1.

8. The process according to claim 7, wherein the comprimates are tablets.

9. The pharmaceutical composition according to claim 1, wherein the composition has water content of less than 6%.

10. The pharmaceutical composition according to claim 1, wherein said composition has a water content of over 10% by weight.

11. The pharmaceutical composition according to claim 9, wherein said composition contains a mixture of microcrystalline cellulose and mannitol as a filler.

12. The pharmaceutical composition according to claim 10, wherein said composition contains a mixture of microcrystalline cellulose and one or several fillers selected from the group consisting of calcium sulfate dihydrate, calcium chloride dihydrate and magnesium trisilicate.$xH_2O$.

13. The pharmaceutical composition according to claim 9, wherein the composition has a water content of 5.9% or less.

14. The pharmaceutical composition according to claim 9, wherein the composition has a water content of 2.5% or less.

15. The pharmaceutical composition according to claim 10, wherein the composition has a water content that ranges from 10.5% by weight to 20% by weight.

16. The pharmaceutical composition according to claim 10, wherein the composition has a water content that ranges from 10.5% by weight to 15% by weight.

17. The pharmaceutical composition according to claim 10, wherein the composition has a water content that ranges from 12% by weight to 18% by weight.

* * * * *